United States Patent [19]

Callahan

[11] 4,363,143
[45] Dec. 14, 1982

[54] INTRAOCULAR LENS

[76] Inventor: Wayne B. Callahan, 1135 Scenic Dr., Milton, W. Va. 25541

[21] Appl. No.: 300,594

[22] Filed: Sep. 9, 1981

[51] Int. Cl.³ .............................................. A61F 1/16
[52] U.S. Cl. ...................................................... 3/13
[58] Field of Search ......................................... 3/13, 1

[56] References Cited

U.S. PATENT DOCUMENTS

| | | | |
|---|---|---|---|
| 4,092,743 | 6/1978 | Kelman | 3/13 |
| 4,159,546 | 7/1979 | Shearing | 3/13 |
| 4,174,543 | 11/1979 | Kelman | 3/13 |
| 4,242,760 | 1/1981 | Rainin | 3/13 |
| 4,244,060 | 1/1981 | Hoffer | 3/13 |
| 4,249,271 | 2/1981 | Poler | 3/13 |
| 4,251,887 | 2/1981 | Anis | 3/13 |
| 4,254,510 | 3/1981 | Tennant | 3/13 |
| 4,280,232 | 7/1981 | Hummel | 3/13 |

FOREIGN PATENT DOCUMENTS 2717706 10/1978 Fed. Rep. of Germany ............ 3/13

Primary Examiner—Ronald L. Frinks
Attorney, Agent, or Firm—Cushman, Darby & Cushman

[57] ABSTRACT

An intraocular lens suitable for use as an artificial lens implant including a medial light focusing lens body, a stem protruding from the periphery of the lens body to an outer edge thereof formed as a stem footplate adapted to make contact with eye tissue, and first and second flexible members extending from opposite sides of the stem footplate. The end of each of the flexible members is formed as a flexible member footplate so that the three footplates make contact with eye tissue at equally angularly spaced positions from the center of the lens body.

10 Claims, 3 Drawing Figures

# INTRAOCULAR LENS

BACKGROUND OF THE INVENTION

This invention relates to intraocular lenses suitable for use as artificial lens implants.

There are many known structural arrangements for intraocular lenses. Some of these are disclosed in the following U.S. Patents, the disclosures of which are incorporated by reference:

U.S. Pat. No. 4,270,230—Polar (1981);
U.S. Pat. No. 4,249,271—Polar (1981);
U.S. Pat. No. 4,244,060—Hoffer (1981);
U.S. Pat. No. 4,174,543—Kelman (1979);
U.S. Pat. No. 4,092,743—Kelman (1978);
U.S. Pat. No. 4,159,546—Shearing (1979);
U.S. Pat. No. 4,014,049—Richards et al (1977);
U.S. Pat. No. 4,073,014—Polar (1978);
U.S. Pat. No. 3,975,779—Richards et al (1976);
U.S. Pat. No. 3,913,148—Potthast (1975);
U.S. Pat. No. 3,906,551—Otter (1975);
U.S. Pat. No. 3,866,249—Flom (1975);
U.S. Pat. No. 3,673,616—Fedorov et al (1972);

Despite these many known lens designs, the "ideal" artificial lens implant had still not been found. Ideally, an artificial lens implant would have a universal size, i.e., one size of lens implant would be suitable for implantation into any human eye within a normal range of sizes. Using such a universal size, a surgeon would not have to stock a variety of sizes of lenses to be selected only after surgically opening an eye for implant. Secondly, the artificial lens would exhibit a high degree of stability within the eye. That is, it would not be displaced in position by the everyday traumas to the eye. Thirdly, the implant would be relatively easy and safe to insert and withdraw from the eye. Fourthly, regardless of the size of the eye into which the artificial lens is inserted, it would exert a relative constant force against the eye tissue and that force would be predictable.

The lens disclosed by the prior issued U.S. patents, listed above, do not meet all of these criteria.

SUMMARY OF THE INVENTION

Therefore, the present invention provides an intraocular lens suitable for use as an artificial lens implant that comes closer than known intraocular lens in meeting the "ideal" design criteria. The lens of the present invention is of one-piece construction and is structured so that one size implant can be used for the normal range of human eye sizes. It exhibits a high degree of stability within the eye because it is formed with a support structure having three points of support in contact with eye tissue spaced at angular intervals of 120° from one another around the center of the lens body.

The lens includes a medial light focusing lens body having a predetermined diameter and thickness and having a generally circular periphery and a stem protruding from the periphery of the lens body to an outer edge thereof formed as a stem footplate adapted to make contact with eye tissue. First and second flexible members extend from opposite sides of the stem substantially at the stem footplate, the end of each of the first and second flexible members being formed as a flexible member footplate for making contact with eye tissue at respective points substantially 120° from the outer edge of the stem. The three footplates form a three-point equally spaced support system for the lens body.

Thus, the lens support structure is formed by one rigid member (the stem) and two very flexible members having terminations approximately 120° on each side of the rigid stem member. Due to the extreme amount of flexure provided in these two flexible members, one size of lens should fit any anterior chamber of a human eye. Furthermore, based on the flexure of the flexible members and their length, the force exerted by eye tissue does not vary substantially within a range of eye sizes.

The same lens periphery shape modified so that the posterior surface is kept flat or angulated toward the anterior surface thereof can be used in the posterior chamber of the eye. A lens of similar shape and smaller in overall dimensions can be implanted into the capsular sac of an eye.

A BRIEF DESCRIPTION OF THE DRAWINGS

The invention will be further described with reference to three Figures wherein.

DETAILED DESCRIPTION OF THE PREFERRED EMBODIMENT

Figure 1:
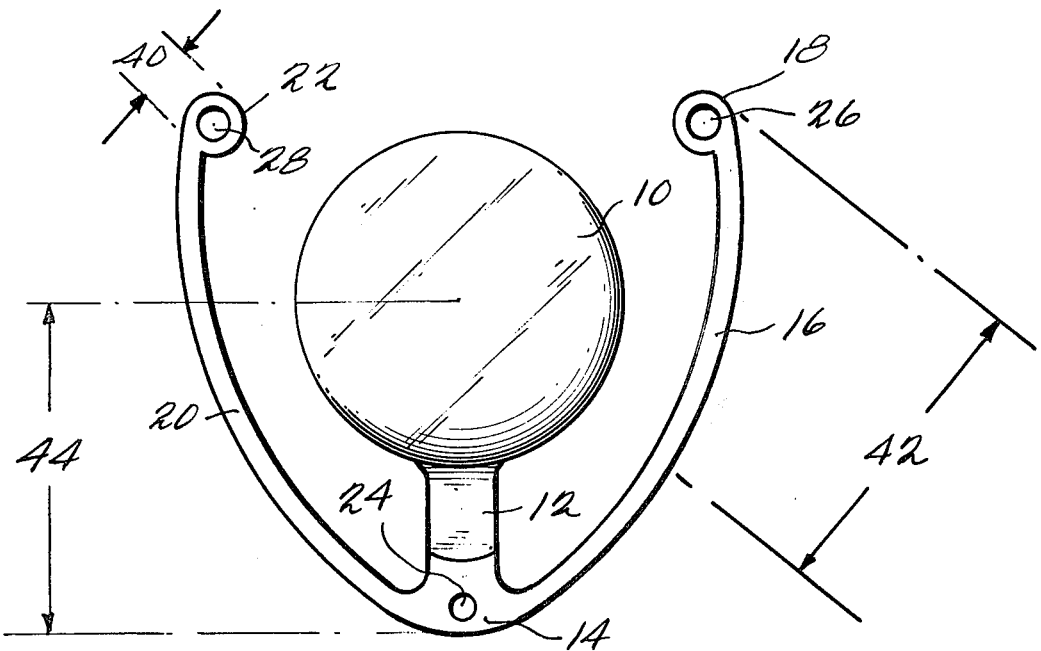
FIG. 1 is a top view of the intraocular lens according to the present invention.

Referring now to FIG. 1 there is shown a top view of the intraocular lens according to the present invention. This lens, fabricated in an appropriate overall size, can be implanted to either the anterior chamber, posterior chamber or posterior capsule of a human eye. It is preferred that the lens be manufactured from a synthetic material capable of providing good optical characteristics while being non-toxicogenic and physiologically inert. One such material would be polymethylmethacrylate. The lens can be shaped by molding, lathe cutting or any suitable method of manufacture.

The lens comprises a medial light focusing lens body 10. The lens body 10 can be formed to a desired predetermined diameter and thickness. Typically, lens body 10 would be in the range of 4 to 7 millimeters in diameter and 0.10 to 0.4 millimeters in thickness. Protruding from the periphery of lens body 10 is a stem 12. Stem 12 is also fabricated to a predetermined thickness and width. A typical range of thickness would be 0.10 to 0.4 millimeters. A typical width would be 0.15 to 3.0 millimeters. The length of the stem would be a function of the size of lens body 10. From the center of lens body 10 to the outer edge of stem 12 the stem length would typically be in the range of 5 to 7 millimeters. For a lens to be implanted in the eye's anterior chamber, the nominal length from the center of lens body 10 to the outer edge 14 of stem 12 would be approximately 6.5 millimeters. The outer edge 14 of stem 12 is formed as a stem footplate 14 for making contact with eye tissue.

As shown in FIG. 1, extending from the right side of stem 12 is a first flexible member 16, the termination of which is formed as a footplate 18. Extending from the left side of stem 12 is a second flexible member 20 terminated in a footplate 22. Footplates 18 and 22 are intended to make contact with eye tissue at points approximately 120° angularly measured from a line running from the center of lens body 10 to the outer edge 14 of stem 12. The three contact points with human eye tissue formed by stem footplate 14 and flexible member footplates 18 and 22 constitute a three-point support system wherein the support positions are equally angular spaced from the center of lens body 10.

Footplates 18 and 22 are generally circular as to form a pad on which eye tissue can rest. Bores 24, 26 and 28 are respectively formed in stem footplate 14, and the flexible member footplates 18 and 22 for two purposes. First, these bores reduce the weight of the lens and secondly they provide a surgeon with a convenient point from which the lens can be manipulated during implantation or removal. For example, the lens can be grasped with a surgical implement through any of these bores, or a suture can be passed through bores so that they could be drawn together and flex either or both of flexible members 16 and 20.

Figure 2:
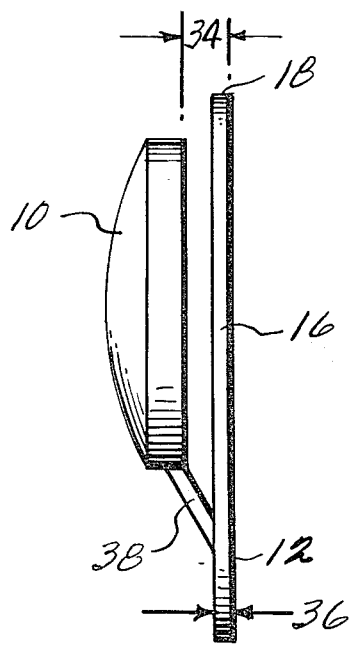
FIG. 2 is a left elevational view of the intraocular lens according to the present invention.
Figure 3:
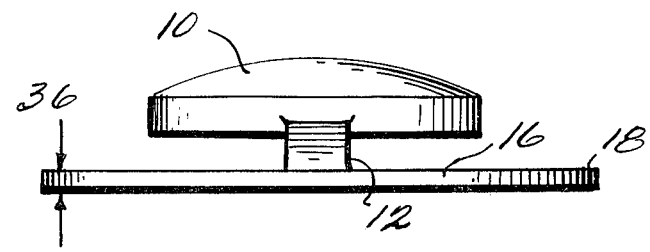
FIG. 3 is a front elevational view of the intraocular lens according to the present invention.

Referring now to FIGS. 2 and 3 there are shown right side and front elevations, respectively. These views illustrate the dimensional interrelationship of the various elements of the intraocular lens. The distance from the edge of a posterior side of stem footplate 14 from the edge of the posterior side of footplate 18 or 22 to the posterior side of lens body 10 is referred to as vault 34 of the lens. The vault on a lens designed for anterior chamber implantation will be in the range of 0 to 0.7 millimeters. A typical range of values would be 0.4 to 0.6 millimeters. The thickness 36 of a footplate 18 or 22 stem footplate 14 will vary within the range of 0.10 to 0.4 millimeters. The angulated portion 38 of stem 12 (most clearly shown in FIG. 2) may be somewhat thicker. The width 40 of a footplate typically will vary from 0.5 to 2 millimeters. The distance 42 from the center of lens body 10 to the outer edge of the footplates is preferably somewhat longer than the radius of the largest eye the lens would be inserted into. This extra length allows for the lens being slightly off-center when the eye is larger than nominal. The distance 44 from the center of lens body 10 to the edge of footplate 14 should be the same as the radius of a nominal size eye for which the lens is intended.

The intraocular lens according to the present invention is particularly suitable for easy surgical implantation. Because the state of the art of surgical implantation of artificial lenses by qualified ophthalmic surgeons is quite high, only a basic insertion method and final positioning of this particular lens design will be discussed.

It is expected that an incision would be made along the cornea-sclera boundry. With many of the prior art rigid lens having members longer than the lens body, it is required that the incision be made longer than necessary to insert only the lens body. According to the structure of the present invention, the two thin flexible members 16 and 18 exhibit the characteristics of a spring. Since foot plates 18 and 22 are attached to the respective flexible thin members, the spring action holds the footplate into position.

For anterior chamber lens implants, the surgeon may choose to insert outer edge footplate 14 first. Using this approach, the flexible members 16 and 18 are compressed towards lens body 10 and pass through an opening sized to allow insertion of lens body 10. The lens is inserted until footplate 14 is resting in a groove formed by the sclera spur and the iris. As footplates 18 and 22 enter the eye and clear the incision, they will spring open until they reach the continuation of the same groove into which footplate 14 was inserted. By attaching a suture through the bored portion of the flexible member footplates, and drawing the footplates together, the lens may be inserted in the opposite orientation as aforementioned.

For posterior chamber lens implantation, if stem 12 is inserted first, footplate 14 will come into contact with a groove formed by the cilinary body and the iris. Once the lens is in this position, the surgeon may slip the remaining footplates behind the iris. Due to the spring action of flexible members 16 and 18 they should come to rest in the continuation of the same groove.

By attaching a suture through the bored portion of the flexible member footplates, and drawing the footplates together, the lens may be inserted in the opposite orientation as aforementioned.

To implant the lens in the posterior chamber capsular sack, the lens can be inserted from either direction and placed into the capsular sack similar to the previously outlined procedure for the posterior chamber lens implantation.

While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

I claim:

1. An intraocular lens suitable for use as an artificial lens implant, comprising:
    a medial light focusing lens body having predetermined diameter and thickness and having a generally circular periphery;
    a stem protruding from the periphery of the lens body to an outer edge thereof formed as a stem footplate adapted to make contact with the eye tissue;
    first and second flexible members extending from opposite sides of the stem substantially at the outer edge thereof from the lens body;
    the end of each of the first and second flexible members being formed as flexible member footplates for making contact with eye tissue at respective points substantially 120° from the outer edge of the stem, the three footplates forming a three-point equally spaced support system for the lens body.

2. A lens according to claim 1 wherein the footplates are formed as circular members with a bore therein to reduce the weight thereof and provide a surgeon with a point to grasp during implantation or removal of the lens.

3. A lens according to claim 1 wherein the diameter of the lens body is in the range of 4–7 millimeters.

4. A lens according to claim 1 wherein the thickness of the lens body is in the range of 0.10 to 0.4 millimeters.

5. A lens according to claim 1 wherein the length from the center of the lens body to the outer edge of the stem is in the range of 5–7 millimeters.

6. A lens according to claim 5 wherein the lens is intended for anterior chamber implantation and the length from the center of the lens body to the outer edge of the stem is approximately 6.5 millimeters.

7. A lens according to claim 1 wherein the footplates have a thickness in the range of 0.10 to 0.4 millimeters.

8. A lens according to claim 1 wherein the footplates have a width in the range of 0.5 to 2 millimeters.

9. A lens according to claim 1 wherein the lens is fabricated in one-piece construction.

10. A lens according to claim 9 wherein the lens is fabricated of polymethylmethacrylate or other suitable material.

* * * * *